United States Patent [19]

Ryan

[11] 4,331,862
[45] May 25, 1982

[54] METHOD FOR CALIBRATING A PARTICLE COUNTING MACHINE AND A CALIBRATION STANDARD THEREFOR

[76] Inventor: Wayne L. Ryan, 3631 S. 116th Ave., Omaha, Nebr. 68144

[21] Appl. No.: 14,603

[22] Filed: Feb. 23, 1979

[51] Int. Cl.$^3$ ............................................. G06M 11/00
[52] U.S. Cl. ................................... 235/92 PC; 73/1 R
[58] Field of Search ...................... 235/92 PC, 92 CA; 324/71 CP; 73/1 R, 432 PS, 1 G, 3, 4 R; 23/230 B

[56] References Cited

U.S. PATENT DOCUMENTS

| | | | |
|---|---|---|---|
| 1,118,981 | 12/1914 | Wenzelmann | 73/1 B |
| 3,412,037 | 11/1968 | Gochman et al. | 73/1 R |
| 3,634,868 | 1/1972 | Pelavin | 73/1 R |
| 3,791,192 | 2/1974 | Butler | 73/1 R |
| 3,874,850 | 4/1975 | Sorensen et al. | 235/92 PC |
| 3,975,727 | 8/1976 | Mader et al. | 73/1 R |
| 4,160,644 | 7/1979 | Ryan | 23/230 B |
| 4,193,288 | 3/1980 | Berber et al. | 73/1 R |

OTHER PUBLICATIONS

"*Lyman Shotshell Handbook*", First Complete Edition, 1969, pp. 26–27 "Powder and Shot Bushings".

*Primary Examiner*—Joseph M. Thesz
*Attorney, Agent, or Firm*—Larson and Taylor

[57] ABSTRACT

A calibration method and standard for calibrating particle counting instruments such as blood platelet counting instruments in which the particles have a distribution of sizes, wherein the method includes the following steps performable in any order. A first known concentration of particles having a mean size which is substantially near the lower extreme size distribution of particles normally counted by the instrument being calibrated are counted and the counts thus obtained are compared with the known count of the concentration. A second known concentration of particles are then counted with the instrument to be calibrated in which the mean size of the second particles is substantially near the upper extreme size distribution of the particles normally counted by the instrument. The count thus obtained is then compared to the known count of the concentration.

14 Claims, 1 Drawing Figure

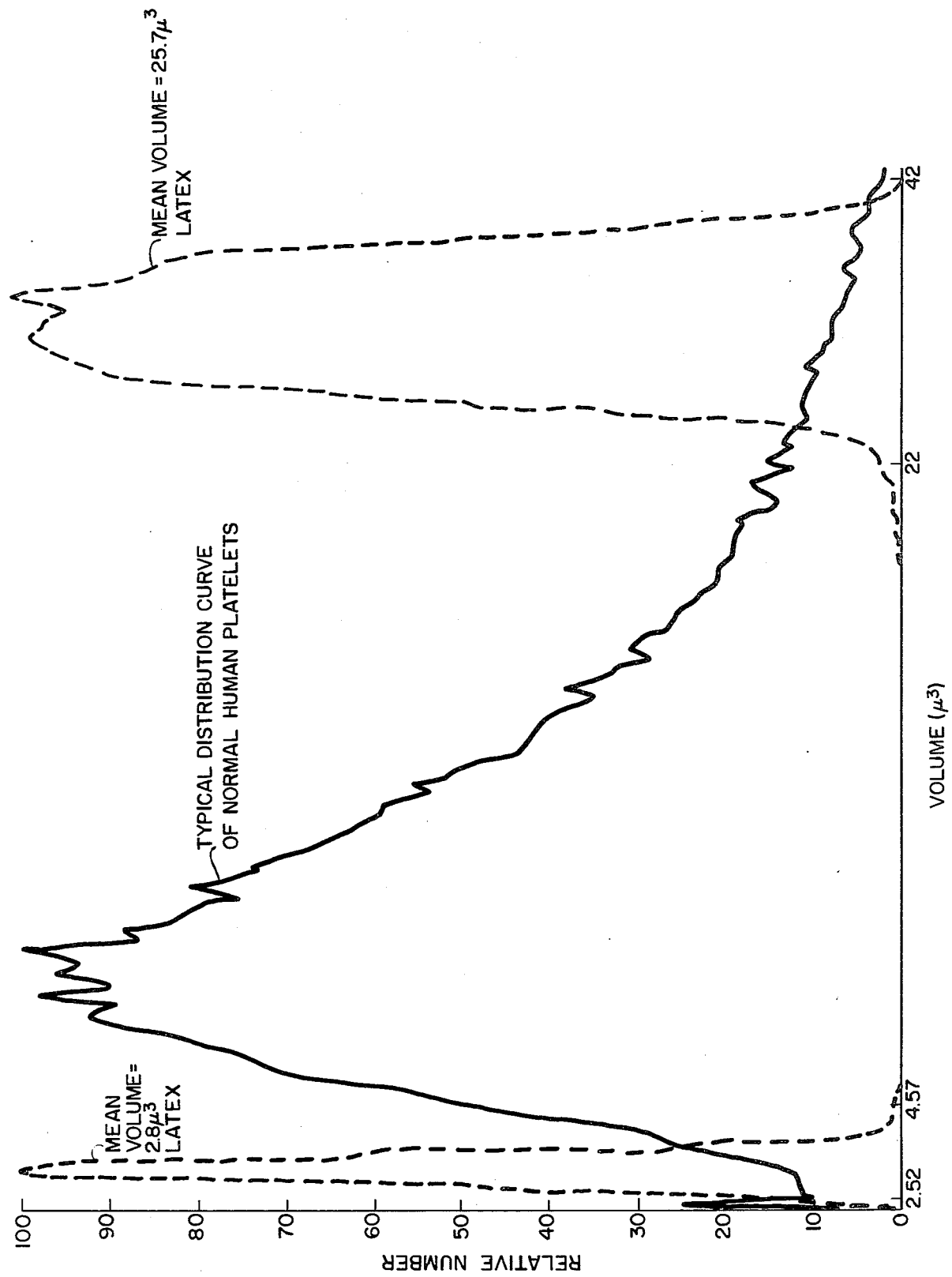

METHOD FOR CALIBRATING A PARTICLE COUNTING MACHINE AND A CALIBRATION STANDARD THEREFOR

FIELD OF THE INVENTION

This invention relates to the calibration of instruments used to count the number of particles suspended in a liquid medium. More particularly, the present invention relates to the calibration of blood platelet counting instruments.

BACKGROUND OF THE INVENTION

There are a large number of different methods to count platelets in whole blood. Platelets can be counted under the phase microscope or light microscope. In addition, platelets can be counted by a variety of electronic instruments or particle counters. The two types of particle counters which are generally, commercially available are those which count particles by conductivity and those that employ light refraction to obtain the particle count. Typical commercially available counters include the "COULTER" ZBI Counter, the $F_n$ Counter and the $Z_f$ Counter from Coulter Electronics; the HPC-103 Counter from Hycel; and the TOA Platelet Counter PL-100. In addition, there is a light-dispersion type counter from Technicon Auto Counter ® and the MK-4/HC ® marketed by J. T. Baker.

Normal blood platelets range in size from $2\mu^3$ to $40\mu^3$ and in certain disease states they may be even larger. Consequently, for the automated counters to accurately count the number of platelets in the blood, they should count all platelets between 2 to $40\mu^3$ inclusive. Many of the commercially available instruments must be frequently calibrated to insure that only the proper size of particles are counted.

At present, manufacturers of these instruments set the instrument thresholds by using only a single standard of particles that have a known volume. For example, red blood cells have a volume of approximately $85\mu^3$. Quite often, these red blood cells are used to calibrate the instrument. Naturally, it can be seen that an instrument calibrated for red blood cells will not necessarily be calibrated for counting platelets. Other instrument users and manufacturers use a latex particle having a radius of 2.02 which provides a particle volume of approximately $4.3\mu^3$. This latter type of calibration principle using only one known point, assumes that the relationship between the settings and the volume is linear and the instruments are adjusted accordingly. However, this procedure of adjusting the instrument may take up to eight hours, depending upon the particular type of instrument being adjusted. Unfortunately, even after spending all this time, the instrument user or manufacturer still does not have an instrument that is accurately calibrated and which gives precise readings throughout the range for counting blood platelets.

Some of the commercially available instruments have thresholds that are preset at the factory and some are adjustable by the user. The problem of the improperly set instrument has become clear as the result of data obtained by the College of Pathologists and the report by Wertz and Koepke, "A Critical Analysis of Platelet Counting Methods", 68 American Journal of Clinical Pathology 195 (July 1977). Thus, it is well known that there is a problem to simply and quickly calibrate particle counting instruments which count extremely small particles having blood platelet sized volumes. However, the problem is perhaps more than just improperly set instruments and perhaps extends to an inability to determine if the instrument is calibrated or not. For example, in one of the many proficiency tests periodically taken and which was reported in the U.S. Department of Health, Education and Welfare, public health service report entitled, "Proficiency Testing Summary Analysis; Hematology 1977 II, Platelet Counting" (December 1977), the reported results revealed that the count of three reference samples expressed as number of platelets$\times 10^9/1$ varied from 234 to 750 for a sample having a reference mean count of 452 and a reference median count of 454, varied from 25 to 174 for a sample in which the reference count at a mean and a median of 76, and varied in a third sample from 76 to 442 for a sample in which the reference mean was 243 and the reference median was 232. Because the participating laboratories know that they were counting a test sample, it must be assumed that they used only calibrated instruments and that their results were thought to be accurate, however, the data received from the survey clearly indicates that the majority of the participating laboratories unknowingly had incorrect results which, in some cases, were off by a factor of 2.

Although particle counting systems are well known and commercially available, the problems typically present in these systems are discussed in the U.S. Pat. Nos. 3,392,331 to Coulter; 3,757,213 to Coulter et al; and 3,944,791 to Baxter; and in the references cited therein, all of which are incorporated herein by reference. On the other hand, U.S. Pat. Nos. to Gochman et al, 3,412,037; to Tate, 3,607,783; and to Butler, 3,791,192 disclose other problems of obtaining a calibration standard and are all incorporated herein by reference.

In summary, although platelet reference controls are a means for determining the reproducibility of pipeting and diluting procedures, they are not easily used to determine the appropriate settings for the counting instruments. This is because the reference control, like normal platelet-rich plasma, and like the conventional calibration standards, do not have an adequate concentration of particles at the upper and lower sizes.

It is noted that many of the commercial counting instruments are provided with means for adjusting the lower and upper threshold counts. It should be apparent, therefore, that the instruments must be adjusted to count all the particles within the known size distribution. If the instrument is adjusted to count particles having a size below the lower extreme size distribution, then other particles and perhaps electronic noise will be added to the true particle count. On the other hand, if the upper threshold level of the instrument is adjusted too high, an incorrect count may result from other particle impurities that may be present in the mixture being counted. Finally, if the upper and lower threshold settings are adjusted too low and too high, respectively, a threshold window that is too narrow will result and not all of the particles thought to be counted will actually be counted. Again, an incorrect and/or inaccurate count will be obtained.

It should also be apparent that any particle and carrier combination selected must be stable so as to avoid disintegration of the particles or the aggregation of two or more particles. If the particle size diminishes from disintegration or increases from aggregation, the particle may be too small or too large (i.e, fall outside the lower or upper threshold sizes) for the counting instrument to count. On the other hand, even if the resulting size of the smaller or larger particle does fall within the size capable of being counted by the instrument (i.e, within the threshold window), a different number of particles will be present in the standard than originally determined. Degradation of the particles can result not only from the instability of the substance from which the particle is made, but also from storage at improper environmental conditions and contamination from fungi and bacteria. The calibration standard can further be contaminated from the mechanical characteristics of the carrier in which the particles are suspended. An improper carrier may result in stratification of the particles or other types of uneven distribution of the particles in the carrier. Also, easy bubble formation would be an undesirable mechanical characteristic of the carrier. Finally, it should be obvious that the carrier must be stable over a wide range of environmental conditions and over a sufficient length of time.

SUMMARY OF THE INVENTION

Accordingly, it is an object of the present invention to overcome the aforementioned and other disadvantages of the conventional prior art calibration methods and calibration standards used therewith. It is also an objective of the present invention to provide a method of calibration and a calibration standard which would result in a rapid test of counting instrument calibration and permit the proper adjustment of the instruments so as to both obtain the proper threshold settings and to obtain the proper count within the desirable threshold window. In one particular embodiment of the invention, the method of calibration and the calibration standard is provided for counting instruments which count extremely small particles having a size on the order of microns (i.e., micrometers).

A calibration method and calibration standard according to the present invention also provides an extremely accurate way to test whether a counting instrument is counting all of the particle sizes within the generally accepted size range of the particles sought to be counted. In addition, those instruments having adjustable electronics can be accurately adjusted so that only those particles as well as all of such particles within the desired size distribution are counted.

A method for calibrating an instrument according to the present invention wherein the instrument is used to count a plurality of particles having a particle size distribution that extends between a lower extreme size distribution and an upper extreme size distribution comprises in any order counting a first known concentration of particles and a second known concentration of particles with the instrument to be calibrated. The first known concentration of particles have a mean size of particles that is substantially near the lower extreme size distribution and the mean size of the second particles is substantially near the upper extreme size distribution. The instrument is calibrated when the counts of the first counted concentration and of the second counted concentration are respectively compared with the counts of the first known concentration and the second known concentration.

In one preferred embodiment of the method for calibrating an instrument according to the present invention, the instrument is used for counting human blood platelets wherein the platelets having known volume distribution from a lower extreme size distribution of about 2 cubic micrometers to an upper size distribution of about 40 cubic micrometers. The method comprises counting a first known concentration of particles with the instrument whereby the mean volume of the first particles in about 2-3 cubic micrometers and counting a second known concentration of particles with the instrument to be calibrated whereby the mean volume of the second particles is about 25-26 cubic micrometers. The instrument is calibrated when the counts of the first and second counted concentrations are respectively compared with the counts of the first and second known concentrations.

A two-pack calibration standard system according to the present invention which is usable for calibrating an instrument to count a plurality of particles having a particle size distribution that extends between a lower extreme size distribution and an upper extreme size distribution comprises essentially a first and second pack. The first pack comprises a known number of first particles having a known mean particle size that is substantially near the lower extreme size distribution and further comprises a carrier comprised of an inert liquid preferably water and a non-ionic surfactant. The second pack comprises a known number of second particles having a known mean particle size that is substantially near the upper extreme size distribution and further comprises a carrier comprised of an inert liquid preferably water and a non-ionic surfactant.

Other objects, features, and advantages of the present invention are discussed in or apparent from the description of presently preferred embodiments of the invention found hereinbelow.

BRIEF DESCRIPTION OF THE DRAWING

The sole FIGURE is a graph of the relative numerical distribution of particle volumes of typical, normal human blood platelets with superimposed graphs of the relative numerical distribution of the particle volumes of calibration standards having respective mean volumes at the lower and upper extreme size distributions of the human blood platelets.

DESCRIPTION OF THE PREFERRED EMBODIMENTS

It has been found that in order to properly calibrate a counting instrument, the instrument must be adjusted to count all the particles having a size within the expected size range. Usually, the distribution of particle sizes follows a typical Gaussean distribution whereby the distribution curve has a lower extreme distribution comprising a relatively small percentage of the total particles, a central, relatively large peak within which the mean particle size is located, and an upper extreme particle size distribution which also comprises a relatively small percentage of the particles. Such a typical particle size distribution exists for human blood platelets, the graph of which is shown in the solid line in the FIGURE. It should be understood, however, that the present invention is not limited to this particular shape of distribution curves, but also includes other distribution curves. Such distribution curves could be bimodal or even trimodal. However, it is important for the use of the present invention that the distribution of particle size be such that there is an upper extreme distribution which comprises a relatively small percentage of the total number of particles and a lower extreme size distribution which likewise comprises a relatively small percentage of the total number of particles.

The present invention provides two calibration standards for calibrating the counting instrument, one calibration standard having a distribution of particles with a mean size that approximates the lower extreme of the size distribution and the other calibration standard having a known distribution of particles with a means size that approximates the upper extreme particle size distribution. As used herein, it is to be understood that the word "calibration" or forms thereof refer very broadly to the checking for the accuracy of an instrument and can refer to merely a go-no-go test of the instrument or an involved adjustment of the instrument such that the instrument indicates the known count of the calibration standard.

The size distributions of particles in a first calibration standard for the lower threshold calibration of a human blood platelet counting instrument and in a calibration standard for the upper threshold calibration of the instrument are graphically depicted in the FIGURE in dashed lines. The graph of the smaller particles of the lower threshold calibration standard is depicted on the left in the FIGURE and shows that the smaller particles have a mean volume of $2.8\mu^3$ and a volume range of about $2.5\mu^3$ to $4.6\mu^3$. The graph of the larger particles of the second, lower threshold calibration standard is depicted on the right in the FIGURE and shows that the larger particles have a mean volume of 25.7 and a volume range of about $22\mu^3$ to $42\mu^3$. In another batch of smaller and larger particles, it was found that the smaller particles had a mean diameter of $1.74\mu$ with a range of diameters of about $1.69\mu$ to $2.06\mu$, and had a mean volume of about $2.76\mu^3$, with a range of volumes of about $2.52\mu^3$ to $4.57\mu^3$. The larger particles had a mean diameter of about $3.66\mu$ with a range of diameters of about $3.48\mu$ to $4.32\mu$, and had a mean volume of about $25.64\mu^3$ with a range of volumes of about $21.98\mu^3$ to $42.10\mu^3$. In any event, as can be clearly seen from the FIGURE, the known mean size of the smaller particles in the first calibration standard is substantially near the lower extreme size distribution of the blood platelets normally counted by the instrument being calibrated, and the known mean size of the larger particles in the second calibration standard is substantially near the upper extreme size distribution of the blood platelets normally counted by the instrument.

The preferred particles in both the upper extreme calibration standard and the lower extreme calibration standard are preferably comprised of a stable, inert substance such as an elastomeric natural or synthetic rubbery material generically referred to as a latex material. The particular type of latex material selected is also a function of the desired particle size. The presently preferred latex materials for the upper standard and the lower standard include a copolymer of styrene and methylstyrene, respectively. However, other stable inert synthetic plastic materials such as polyvinyl chloride and polypropylene can also be used. Also, ceramic materials can be used. Obviously, the material selected will depend in part upon the size of the particle desired. For example, styrene is preferred for particles having volumes in the order of cubic micrometers and a copolymer of styrene and methylstyrene is preferred for particles having volumes in the order of tens of cubic micrometers. These particles have been found to have a six-month stability when stored at conventional room temperature of 25° C. In addition, such particles are inert with respect to the carrier in which they are diluted and with respect to the test probe of the counting instrument.

The carrier used as the diluent or suspension medium for the particles must be chemically and physically compatible and usable with the selected particle material and with the type of counting instrument. Thus, for use in those counting instruments which utilize the change in electrical conductivity to calculate the count, the carrier must be electrically conductive. This type of counting instruments constitutes a large majority of those on the market today and include the aforementioned Coulter ZBI and Fn counters. On the other hand, for those counting instruments which utilize the light scattering principle, the carrier must be optically conductive (or transparent, i.e., have a very low absorption coefficient). As mentioned above, the Technician Auto Counter ® is such a counting instrument. Preferably, the carrier is an aqueous solution, although any inert, stable liquid, such as toluene, could be used.

Those skilled in the art who use counting instruments employing the principle of electrical conductivity are aware that the conductivity of the carrier will greatly affect the indicated count of the instruments. Thus, a standard carrier conductivity has been adopted and is the conductivity of 0.8% to 0.85% equivalent molarity of sodium chloride.

It has been found that the stability of the carrier can be greatly enhanced if an appropriate surfactant is added thereto. Preferably, such a surfactant is non-ionic so that the aggregation of particles is minimized and is present in the minimum amounts necessary. Too great a percentage of surfactant in the carrier results in the formation of bubbles and too little does not provide the desired degree of stability.

The concentration of the surfactant can be in the range of about 0.059% to 0.3% and a preferable concentration is approximately 0.2%. The polyoxethylene-polyoxypropylene block polymers are a presently preferred surfactant and are well known in the art and may be represented by the structural formula:

wherein the $(C_3H_6O)_b$ represents the polyoxypropylene hydrophobic base component and the $HO(C_2H_4O)_a$ and $(C_2H_4O)_cH$ represent the polyoxyethylene hydrophilic constituents. The polyoxyethylene portion of the polymer may vary from as little as 10 percent to as high as 90 percent. The higher the polyoxyethylene percentage, the more water-soluble becomes the total molecule or polymer. The substantially water-soluble polymers in the molecular weight range of between about five and about eleven thousand are preferable. These materials are readily available under the trade name Pluronic polyols. A preferred material of this class for use in the compositions of this invention is available under the trade name of Pluronic F88 and has an average molecular weight of about 11250, although it may vary in range between about 9000 and 16000. In this material, a, b and c in the above formulas can, for example, be present in weight ratio of 80% of a plus c and 20% of b. Also, the molecular weight of the polyoxypropylene hydrophobe is about 2250. The characteristics, composition and method of manufacture of such Pluronic series of surfactants are disclosed in U.S. Pat. No. 3,730,960, in the 1973 pamphlet entitled, "The Wonderful World of Pluronic Polyols", published by BASF Wyandotte Corporation, Library of Congress Catalog Card No.

70-150738, and in British Pat. No. 759,295 to the General Aniline and Film Corporation.

In order to maximize the life of the calibration standard and to prevent aggregation of the particles, it is important that the pH of the carrier be compatible with the particles and other additives in the carrier. For example, it has been found that a ph falling generally within the range of 6.0 to 8.0 is acceptable and that a preferable range is from 6.9 to 7.3 with a pH of 7.2 having been found to be most preferable for use with particles of a latex material. If the pH of the carrier is either too high or too low, it has been found that the latex particles may aggregate, thereby diminishing the total number of particles in the standard and further increasing the size of the aggregates to perhaps a size that would fall outside of the threshold window. It is noted that the term aggregation is used broadly and also includes the formation of doublets or triplets of particles which, it should be appreciated, would be as detrimental as the formation of much larger aggregates of particles.

It is also desirable to include in the carrier a small, but sufficient concentration of a preservative. More particularly, the preservative is preferably a fungicide and/or a bactericide. Although any additive which is compatible with the other components of the carrier and with the particle material is acceptable, it has been found that a preservative selected from the group consisting essentially of phenol, sodium floride and sodium azide is compatible with the other components in the calibration standard and accomplishes the desired result of preventing the growth of bacteria and fungi in the carrier or on the particles. Preferably, the additive selected is phenol and is used in an amount within the range of about 0.05% to 0.25% and preferably 0.1% by weight of the carrier liquid.

A preferable use of a method and calibration standard according to the present invention is for calibrating counting instruments which count blood platelets. With reference to the FIGURE, there is shown a graphical distribution of normal human blood platelets. It can be seen that the volume distribution of the blood platelets extend from a lower mean distribution of about 2.5 cubic micrometers to an upper volume distribution of greater than 42 cubic micrometers. The mean volume of the "normal" platelet-rich human blood plasma is about 8.5 cubic micrometers. Thus, it can be seen to properly set an instrument to count all of the blood platelets in the normal platelet-rich plasma, the instrument must be set to count particles having a volume between 2.5 to at least 40 cubic micrometers.

Although the present invention is directed to a method and a calibration standard for calibrating counting instruments which count blood platelets, the present invention should not be so limited. The present invention is usable for calibrating any counting instrument which counts particles having a size distribution as discussed above. Thus, the present invention is usable to calibrate counting instruments which count bacteria, red blood cells, white blood cells, plant pollen, animal eggs, and the like. The following examples are included to further illustrate the present invention.

EXAMPLE I

A two-pack calibrating standard system for calibrating an instrument to count human blood platelets was prepared by mixing an amount of first particles of polystyrene having a mean volume size of 2.76 cubic micrometers and a range of volume sizes from 2.52 cubic micrometers to 4.57 cubic micrometers and an amount of second particles of a copolymer of styrene and methyl styrene having a mean volume size of 25.64 cubic micrometers and a distribution range of volume size from 21.98 cubic micrometers to 42.1 cubic micrometers with an aqueous carrier. The first particles were of generally spherical shape having a mean diameter of 1.74 micrometers and a range of diameters of 1.69 to 2.06 micrometers and the second particles were of spherical shape having a mean diameter of 3.66 micrometers and a range of diameters of 3.48 to 4.32 micrometers. The carrier was an aqueous solution having the following amount of additives for each 1000 grams of water: 8.84 grams of sodium chloride; 0.19 grams of sodium monobasic phosphate ($Na_2H_2PO_4$); 1.9 grams of sodium dibasic phosphate ($Na_2HPO_4$); 0.3 grams of EDTA (ethylene diamine tetraacetic acid); 2.5 grams of phenol; and 2.0 grams of Pluronic F88 polyol (Pluronic being a trademark of the BASF Wyandotte Corporation).

The total number of particles in each system was about 200,000/$mm^3$, a non-critical amount which is selected simply on the basis as being within the total number of particles which can be counted by the particular instrument. The amount of sodium monobasic phosphate and sodium dibasic phosphate was selected such that together with an added amount of hydrochloric acid a pH of the solution of 7.2 was obtained. With respect to the total number of particles in each system, it is noted that most commercial instruments would require the particles be diluted from 200,000/$mm^3$ by a factor of 1:3000 so that a count of 66 particles/$mm^3$ would be obtained.

EXAMPLE II

The two-pack calibration standard system was used to calibrate a Coulter ZBI, a popular instrument having adjustable thresholds used for counting blood platelets. The instrument was adjusted according to the manufacturer's recommendations. First, the aperture current and amplification settings were adjusted to count platelets, i.e., the aperture current setting is $\frac{1}{2}$ and the amplification is $\frac{1}{4}$. A counting vial with diluting fluid was placed under the aperture tube and the upper threshold dial was turned to 100. Starting at 0 on the lower threshold dial, the dial was moved forward until no counts due to electronic "noise" of the instrument was obtained.

The upper threshold of the instrument was obtained as follows. The second pack for the upper threshold range was vortexed and the contents thereof then poured into the counting vial. The sample was then permitted to stand for five minutes in order to allow air bubbles to dissipate. The lower threshold was then turned to the midpoint on the indicator dial (i.e., set to 50). The upper threshold was set at its maximum (i.e, at 100), and a counting vial with only pure diluting fluid normally used for platelet counting was placed under the aperture tube. The instrument had virtually no counts, which is normal. Then, the counting vial containing the upper threshold standard was placed under the aparture tube and the reading on the instrument was obtained. That count should be 6,500 indicating a concentration of approximately 200,000 particles per $mm^3$. The upper threshold of the instrument was then lowered in intervals with readings taken at each interval. This process was continued until the number of particles obtained was reduced. At that setting, some of the latex particles were not being counted. The upper threshold dial was then moved backwards until the maximum count was again obtained. At this particular setting of the upper threshold dial, the instrument was adjusted to count particles up to about 30 cubic micrometers.

The lower threshold was set by placing a counting vial with the diluting fluid normally used for platelet counting under the aperture tube. The upper threshold value is left as determined above and beginning at 0 on the lower threshold dial, the dial is rotated forward until there are no counts due to electronic "noise" of the instrument. Then, the lower threshold standard was thoroughly mixed and the contents poured into a counting vial. After permitting the lower threshold standard to stand for five minutes to allow any air bubbles to dissipate, the container was then placed under the aperture tube. The lower threshold setting was moved foward at small intervals and the counts at each interval was obtained. When a count less than the original maximum count was obtained, some of the latex particles in the lower threshold standard were not being counted. The lower threshold setting was then moved lower until the maximum count was again obtained. At that setting, the lower threshold was set to count particles greater than 2.5 cubic micrometers.

The count of the number of latex suspensions in each of the lower and upper threshold standards was verified by being counted ten times in a hemacytometer. The suspensions were also examined microscopically and with a Coulter ZBI ® with Channelyzer for aggregate or doublet formation. The suspensions were found to have less than 0.5% aggregates. For use, the upper and lower threshold standards were diluted in accordance with the manufacturer's recommendations for counting platelets in platelet-rich plasma. In the above second Example, 6.6 microliters of latex particles were diluted to 20 ml before counting.

The following instruments were also tested to determine their ability to count the latex particles: Coulter Model ZBI, Coulter Model Fn, Toa Pl-100, Hycel HPC-103; Baker MK-4/HC; and Technicon Autocounter. The results are set forth hereinbelow as Table I. The first count was made using the manufacturer's recommended settings for the instrument and is expressed in Table I as a percent of particles counted. For each threshold standard, two particle concentrations were used, concentration A and concentration B. The particle count for each concentration is given under the hemacytometer count.

TABLE I

| Instrument | | Performance at 2.8 $\mu m^3$ particles; % Recovery of Particle Counts | | Performance at 26 $\mu m^3$ particles; % Recovery of Particle Counts | |
|---|---|---|---|---|---|
| | | Recommended Setting | Optimum Setting | Recommended Setting | Optimum Setting |
| Coulter ZBI | A. | 100 | | 58 | 100 |
| | B. | 100 | | 56 | 100 |
| Coulter FN | A. | 91 | 100 | 85 | 100 |
| | B. | 89 | 100 | 83 | 100 |
| Toa Pl-100 | A. | 71 | 100 | 69 | 100 |
| | B. | 66 | 100 | 66 | 100 |
| Hycel HPC-103 | A. | 71 | 100 | 97 | 100 |
| | B. | 77 | 100 | 89 | 100 |
| Baker MK-4/HC | A. | 50 | | 100 | |
| | B. | 50 | | 100 | |
| Technicon | | | | | |

TABLE I-continued

| Instrument | | Performance at 2.8 $\mu m^3$ particles; % Recovery of Particle Counts | | Performance at 26 $\mu m^3$ particles; % Recovery of Particle Counts | |
|---|---|---|---|---|---|
| | | Recommended Setting | Optimum Setting | Recommended Setting | Optimum Setting |
| Autocounter | A. | 100 | | 100 | |
| | B. | 100 | | 100 | |
| Hemacytometer Count | A. | $303 \times 10^9/1$ c.v. = 13% | | $548 \times 10^9/1$ c.v. = 8% | |
| | B. | $83 \times 10^9 1$ c.v. = 9% | | $172 \times 10^9/1$ c.v. = 11% | |

The Baker and Technicon instruments could not be adjusted and therefore could not be set to read 100% of the particle counts.

The following example is included to illustrate the importance of selecting a non-ionic surfactant.

EXAMPLE III

A number of lots of a calibration standard having different sizes of particles were prepared in which the particles were of the same material as described in Example I and in which the carrier was an aqueous solution having the following amounts of additives: an amount of sodium salts to produce a conductivity equivalent to 0.8% molarity of NaCl and a pH of about 7.2 (see Example I); about 0.2% of the non-ionic surfactant F-88; and about 0.2% of phenol. A stability test at 0° C., 6° C., 25° C., and 40° C. with the counts being obtained by using a Coulter Counter ZBI are shown in Table II hereinbelow.

TABLE II

| | Initial | 1 mo | 2 mo | 3 mo | 4 mo | 5 mo | 6 mo |
|---|---|---|---|---|---|---|---|
| | 1.75µ LATEX* | | | | | | |
| 40° | 205,000 | 204,500 | 205,000 | 206,000 | 210,000 | 206,000 | 205,000 |
| 25° | 205,000 | 205,000 | 204,500 | 204,000 | 205,000 | 206,000 | 205,500 |
| 6° | 207,000 | 206,000 | 206,500 | 206,000 | 207,000 | 208,000 | 208,000 |
| 0° | 210,000 | 207,000 | 208,000 | 211,000 | 209,000 | 210,000 | 208,500 |
| | 3.5µ LATEX* | | | | | | |
| 40° | 201,000 | 202,000 | 201,000 | 201,500 | 203,000 | 202,000 | 200,500 |
| 25° | 198,000 | 199,000 | 201,000 | 200,000 | 199,000 | 199,000 | 200,000 |
| 6° | 200,000 | 200,000 | 200,000 | 201,000 | 200,500 | 200,000 | 201,000 |
| 0° | 198,000 | 198,500 | 198,500 | 198,000 | 198,000 | 200,000 | 198,000 |

*Values rounded off.

The above examples are directed to a method of calibrating and a calibration standard for calibrating conventional blood platelet counting instruments. Obviously, numerous variations of the above-described calibration standard and methods for calibrating instruments that count other particles as well as variations within the above calibration standard and method are within the scope and spirit of the present invention would be apparent to one skilled in the art.

I claim:

1. A method for testing an instrument used to count a plurality of particles having a particle size distribution that extends between a lower extreme size distribution and an upper extreme size distribution to see if it is in calibration, the method comprising in any order:

counting a first known concentration of particles having a known count with the instrument to be calibrated, the mean size of the particles in said first known concentration being substantially near the lower extreme size distribution;

comparing the count of said first counted concentration with the known count of said first known concentration;

counting a second known concentration of particles with the instrument to be calibrated, the mean size of the particles in said second known concentration being substantially near the upper extreme size distribution; and comparing the count of said second counted concentration with the known count of said second known concentration.

2. A method as claimed in claim 1 wherein said first and second known concentrations of particles are each in a carrier comprising water and a non-ionic surfactant.

3. A method as claimed in claim 2 wherein the concentration of said surfactant is in the range of about 0.059% to 0.3%.

4. A method as claimed in claim 2 wherein said surfactant is a polyoxyethylene-polyoxypropylene block polymer.

5. A method as claimed in claim 4 wherein said surfactant has a molecular weight of polyoxypropylene hydrophobe of about 2250 and is about 80% by weight polyoxyethylene.

6. A method as claimed in claim 4 wherein said surfactant concentration is approximately 0.2%.

7. A method as claimed in claim 3 wherein said carrier has a substantially neutral pH.

8. A method as claimed in claim 2 wherein said carrier also includes a fungicide or bactericide.

9. A method as claimed in claim 8 wherein said fungicide is phenol in a concentration of about 0.17% to 0.25%.

10. A method as claimed in claim 1 wherein said particles in both said first and second known concentrations are of an elastomeric, stable material.

11. A method as claimed in claim 10 wherein said first particle is of polystyrene and said second particle is a copolymer of styrene and methylstyrene.

12. A method for testing known blood platelet counting instruments wherein the platelets have a known volume distribution from a lower extreme size distribution of about 2.5 cubic micrometers to an upper extreme size distribution of about 40 cubic micrometers to see if the instruments are in calibration; said method comprising in any order:

counting a first known concentration of particles having a known count with the instrument to be calibrated, the mean volume of said first particles being about 2 to 3 cubic micrometers;

comparing the count of said first counted concentration with the known count of said first known concentration;

counting a second known concentration of particles with the instrument to be calibrated, the mean volume of said second particles being about 25 to 26 cubic micrometers; and comparing the count of said second counted concentration with the known count of said second known concentration.

13. A method as claimed in claim 12 wherein said first particles have a volume distribution from about 2.5 cubic micrometers to about 4.6 cubic micrometers.

14. A method as claimed in claim 12 or 13 wherein said second particles have a volume distribution from about 22 cubic micrometers to about 42 cubic micrometers.

* * * * *